United States Patent [19]
Shibayama et al.

[11] Patent Number: 6,117,648
[45] Date of Patent: Sep. 12, 2000

[54] METHOD FOR THE ACTIVATION OF BLOOD COAGULATION FACTOR XII

[75] Inventors: Yoji Shibayama, Katoh-gun, Japan; Allen P. Kaplan, Charleston, S.C.

[73] Assignee: Nippon Zoki Pharmaceutical Co., Ltd., Osaka, Japan

[21] Appl. No.: 08/925,167

[22] Filed: Sep. 8, 1997

[30] Foreign Application Priority Data

Sep. 12, 1996 [JP] Japan ..................................... 8-265318

[51] Int. Cl.⁷ ..................................................... C12Q 1/56
[52] U.S. Cl. ............................................ 435/13; 435/69.6
[58] Field of Search ...................... 435/13, 69.6; 436/69; 514/12, 21; 530/380, 388.25, 413

[56] References Cited

U.S. PATENT DOCUMENTS

| | | | |
|---|---|---|---|
| 4,985,354 | 1/1991 | Toyomaki et al. | 435/13 |
| 5,560,935 | 10/1996 | Konishi et al. | 424/520 |
| 5,599,683 | 2/1997 | Nishikawa et al. | 435/13 |
| 5,648,228 | 7/1997 | Nishikawa et al. | 435/13 |

FOREIGN PATENT DOCUMENTS

| | | |
|---|---|---|
| 4-14000 | 1/1992 | Japan . |
| 7-51097 | 2/1995 | Japan . |
| 7-51098 | 2/1995 | Japan . |

OTHER PUBLICATIONS

Ghebrehiwet B., Identification of Functional Domans on GC1Q–R, a Cell Surface Protein That Binds to the Globular Heads of C1Q, Using Monoclonal Antibodies and Synthetic Peptides, Hybridoma 15(5):333–342, May 1996.

Kusumam J., Identification of the Zinc Dependent Endothelial Cell Binding Protein for High Molecular Weight Kininogen and F XII, Proc Natl Acad Sci USA 93:8552–8557, Aug. 1996.

Kaplan A., Binding of Activation of Kinin Forming Proteins on Vascular Endothelial Cells, Immunopharmacology 36:201–207, 1997.

Herwald et al., "Isolation and Characterization of the Kininogen–binding Protein p33 from Endothelial Cells", *J. Biological. Chem.* vol. 271, No. 22, 1996, pp. 13040–13047 May 31, 1966.

Ghebrehiwet et al., "Isolation cDNA Cloning, and Overexpression of a 33–kD Cell surface Glycoprotein that Binds to the Globular "Heads" of Clq", *J. Exp. Medicine*, vol. 179, No. 6, 1994, pp. 1809–1821. Jun. 1994.

*Primary Examiner*—Ralph Gitomer
*Attorney, Agent, or Firm*—Hollander Law Firm, P.L.C.

[57] ABSTRACT

Blood coagulation factor XII (FXII) is activated using a receptor for globular heads of the complement component Clq. The receptor (gC1qr) is a protein and provides a more faithful in vitro reproduction of the actual FX-II-activating reaction which occurs in living organisms. The protein receptor, gClqR may be obtained in at least substantially pure or isolated form by recombinant genetic engineering techniques or by isolation from animal cell membranes to which the complement component Clq binds. The receptor may be separated, purified, or isolated from cell membranes. The activation of the blood coagulation factor XII may be conducted in: 1) an animal plasma, 2) a reconstituted plasma kallikrein-kinin system, or 3) an at least substantially pure blood coagulation factor XII. The activation with the receptor is preferably conducted in the presence of zinc ions. FXII may be subjected to an activation reaction with the isolated or at least substantially purified receptor for globular heads of Clq in the presence of a pharmaceutical to evaluate or measure the pharmaceutical's inhibiting or promoting action towards the plasma kallikrein-kinin system, blood coagulation system, fibrinolysis system, renin-angiotensin system, complement system, or arachidonate cascade. The drug screening may include evaluation of a compound's utility as an antiinflammatory agent, an antiallergic agent, or an analgesic.

17 Claims, 2 Drawing Sheets

METHOD FOR THE ACTIVATION OF BLOOD COAGULATION FACTOR XII

FIELD OF THE INVENTION

The present invention relates to a method for the activation of blood coagulation factor XII using a receptor for globular heads of the complement component C1q.

BACKGROUND OF THE INVENTION

A plasma kallikrein-kinin system is a series of reaction systems in vivo producing kinins which have various physiological activities. The plasma kallikrein-kinin system strongly participates in controlling the functions of living organisms. The system has a close relation with various other enzymatic reaction systems such as the renin-angiotensin system, the blood coagulating system, the fibrinolysis system, the complement system and the arachidonate cascade mainly for prostaglandin, leukotriene and thromboxane or catecholamine.

Kinins, such as bradykinin, which are the products of the kallikrein-kinin system have various physiological activities such as hypotension by dilation of peripheral blood vessels, increasing permeability of blood vessels, contraction and relaxation of smooth muscles, generation of pain, migration of leukocytes and liberation of catecholamine from the adrenal cortex. In addition, they are known as mediators for inflammation reactions including allergic reactions whereby their presence in living organisms is greatly significant. Accordingly, it is believed that substances which suppress the actions of kinins or inhibit the production thereof are useful as pharmaceuticals such as antiinflammatory agents, analgesic agents and antiallergic agents.

An initial stage in a series of reaction systems of the plasma kallikrein-kinin system is activation of the blood coagulation factor XII (FXII). When FXII is activated in vivo by injury or by an invading stimulation to tissues or the like, a series of enzymatic reactions of the plasma kallikrein-kinin system proceeds. Thus, the activated FXII (blood coagulation factor XII of an activated form; FXIIa) acts on the plasma prekallikrein existing in the same plasma converting it to plasma kallikrein which is an enzyme of an activated form. Then the resulting plasma kallikrein acts on a high molecular weight kininogen (HMWK) in the plasma whereupon bradykinin having various physiological activities as mentioned above is produced and liberated.

The activating reaction of FXII plays very important roles not only as a reaction for initiating the plasma kallikrein-kinin system but also as a reaction for controlling the initiating steps of various other function-controlling systems in living organisms such as the blood coagulating system, fibrinolysis system, renin-angiotensin system, complement system and arachidonate cascade. FXII has been known to be activated on a heterologous surface having a negative charge. Examples of such heterologous surfaces are kaolin, glass, Celite, dextran sulfate, collagen and acidic mucopolysaccharides. In addition, U.S. Pat. Nos. 5,599,683 and 5,648,228 disclose FXII activation with cell components such as membranes of platelets and other cells, fibronectin, elaidic acid, quercetin, rutin, sulfated glycolipids, proteoglycan, mucopolysaccharides, sodium stearate, dextran sulfate, amylose sulfate, carrageenin and proteases which activate FXII by a restricted decomposition. However, substances which activate FXII in actual living organisms have not yet been specifically identified, purified, or isolated.

The present invention provides a novel FXII-activating method which is different from the conventional method using a heterologous surface having a negative charge. An FXII-activating substance in living organisms is identified, produced in a pure or isolated form, in which interfering or competing components or other factors are substantially or completely absent, for a more faithful reproduction of an actual FXII-activating reaction in living organisms.

The present inventors have conducted an intensive study for an FXII-activating substance existing in living organisms. They have found as a result thereof that a receptor protein for globular heads of C1q which is a complement component existing on cell membranes is a substance which activates FXII whereupon the present invention has been accomplished.

SUMMARY OF THE INVENTION

The present invention relates to a method for the activation of the blood coagulation factor XII (FXII) using a receptor protein (gC1qR) to the globular heads of the complement component "C1q". The present invention also provides an FXII activator which consists of or consists essentially of the protein receptor, gC1qR which may be obtained by recombinant genetic engineering techniques or by isolation from animal cell membranes. The method of the present invention is useful for providing a more faithful reproduction and reflection of the actual FXII-activating reaction in living organisms. Use of an isolated protein receptor or a substantially or completely pure protein receptor eliminates other factors, such as other membrane wall proteins, or components which may interfere or compete with the FXII activation.

The receptor may be separated, purified, or isolated from cell membranes, such as the membranes of endothelial cells, lymphocytes, monocytes, macrophages, neutrophils, eosinophils, fibroblasts, platelets, synovial cells, and mixtures thereof. The cells employed may comprise natural cells, cultured and proliferated cells or tumorigenically transformed cultured cells. Separation of the receptor from the cells may be achieved by solubilizing the cell membrane, and subjecting the solubilized cell membrane to purification by chromatography, preferably affinity chromatography using a carrier obtained by insolubilization of gC1q or high molecular weight kininogen. In other embodiments of the invention, the receptor may be a recombinant gC1qR.

The activation of the blood coagulation factor XII may be conducted using an effective, FXII activating concentration of the receptor in various systems which comprise FXII such as: 1) an animal plasma, 2) a reconstituted plasma kallikrein-kinin system, or 3) an at least substantially pure blood coagulation factor XII. The activation with the protein receptor is preferably conducted in the presence of zinc ions.

In accordance with the present invention, a pharmaceutical or test substance may be evaluated for its inhibiting or promoting action towards the plasma kallikrein-kinin system, blood coagulation system, fibrinolysis system, renin-angiotensin system, complement system, or arachidonate cascade. The blood coagulation factor XII is subjected to an activation reaction with the isolated or at least substantially purified receptor for globular heads of C1q in the presence of the pharmaceutical. The degree of activation of the blood coagulation factor XII may then be quantitatively measured. The drug screening may include evaluation of a compound for utility as an antiinflammatory agent, an antiallergic agent, or an analgesic.

DETAILED DESCRIPTION OF THE INVENTION

Figure 1:
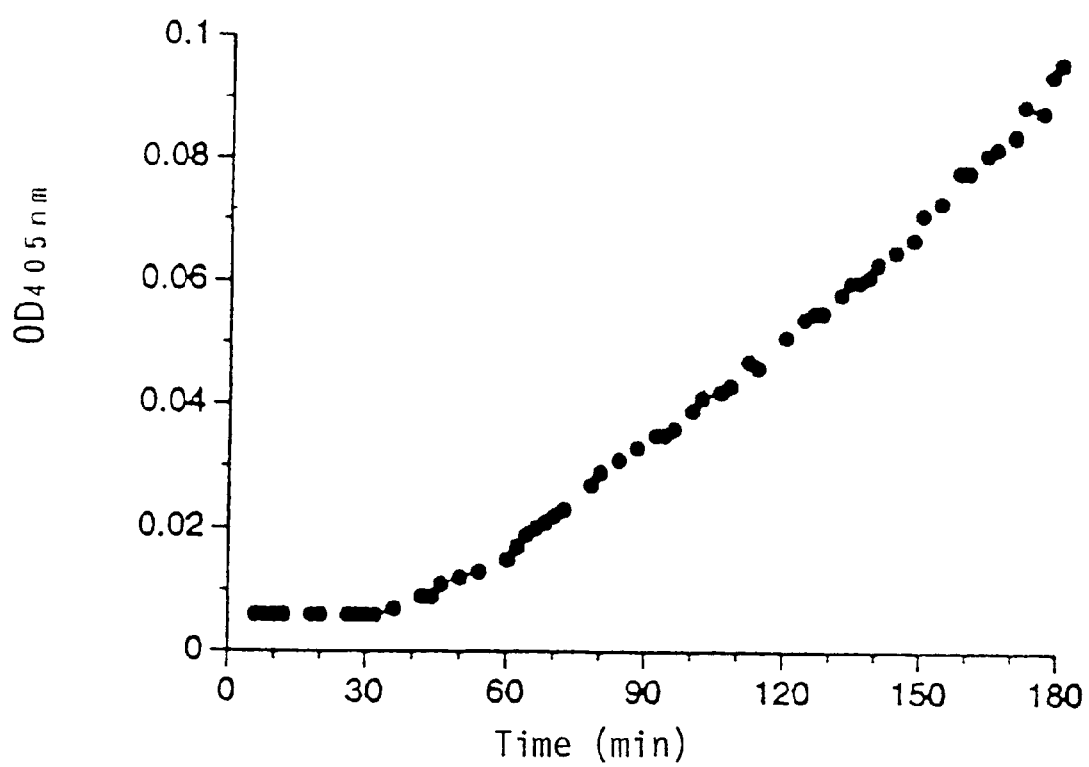
FIG. 1 shows a result of the investigation of Example 2 where FXII and gC1qR were mixed and made to react and the activation of FXII by gC1qR was measured at different lapses of time.

The present invention provides a method for the activation of FXII using a receptor for globular heads of C1q (hereinafter, referred to as gC1qR) and also to an activator for FXII consisting of said substance. "Complement" is a general name for about twenty kinds of serum protein which play an important role as mediators for various immune reactions and allergic reactions. It inherently exists in blood in an inactive form but, when activated by an antigen-antibody complex, membrane components of bacteria or animal cells, etc., it shows various biological activities such as hemolytic or bacteriolytic reaction, promotion of phagocytosis, promotion of inflammation, etc. Activation of the complement is initiated by contacting with the above-mentioned activator (gC1qR) whereby the complement component "C1" is activated. C1q is one of the subcomponents of three kinds of C1. The C1q subcomponent has an activity of binding to various cells such as lymphocytes, monocytes, macrophages, neutrophils, eosinophils, fibroblasts, platelets, endothelial cells and synovial cells. Therefore, the presence of a receptor for C1q on their cell membranes has been suggested and isolated and identified.

The gC1qR used in the present invention can be prepared by separation and purification from cells such as endothelial cells, lymphocytes, monocytes, macrophages, neutrophils, eosinophils, fibroblasts, platelets, synovial cells, and mixtures thereof, of various animals including human beings. With respect to the cells, not only normal ones obtained from the components of living organisms but also cultured and proliferated cells or tumorigenically transformed cultured cells may be utilized. Separation of gC1qR and succeeding purification may be conducted utilizing means which have been commonly used for the purification of membrane proteins. For example, a method wherein a cell membrane is solubilized using detergents followed by purification with various chromatographic means is a known technique which may be employed in the present invention. Affinity chromatography using a carrier obtained by insolubilization of gC1q (globular heads of C1q), HMWK or the like is an especially effective method because it utilizes a biochemical affinity for gC1qR. Thus, it has a high separating ability and is capable of separating the gC1qR from other membrane proteins in a specific manner.

Further, a recombinant gC1qR which is prepared by means of genetic engineering may be used in the FXII-activating method of the present invention too. In accordance with said genetic engineering means, a product which is uniform and contains less contaminant proteins can be easily prepared. The recombinant gC1qR may, for example, be manufactured by a method of B. Ghebrehiwet et al [J. Exp. Med., volume 179, pages 1809–1821 (1994)] herein incorporated by reference in its entirety.

The reaction system in the FXII-activating method of the present invention may be appropriately selected depending upon the object. Thus, a reaction system using common animal plasma containing FXII, a reconstituted system wherein FXII, plasma prekallikrein and HMWK which are constituting components of the plasma kallikrein-kinin system are combined, etc. may be exemplified as basic reaction systems which may be employed. In addition, a reaction system which at least substantially contains only FXII can be utilized in the present invention. It has been confirmed that the FXII-activating method of the present invention using gC1qR is dependent on zinc and it is preferred that all of the above-mentioned reactions are conducted in the presence of an effective amount of zinc ions, although other metal ions may be utilized. For selecting optimum reaction conditions, additives which are commonly used in the related art, such as albumin and saccharides, may be appropriately added to the reaction system in addition to salts such as sodium chloride and buffers. Each of the reaction conditions for the FXII-activating method of the present invention such as effective activating concentrations of gC1qR, FXII, other pure proteins, additives, etc., pH, reaction temperature and reaction time may be those commonly used in the art. They may be investigated and freely selected by those skilled in the art in accordance with their objective or purpose in using the activation.

In order to measure the degree of activation of FXII by the FXII-activating method of the present invention, confirmation can be performed by determining the resulting FXIIa quantitatively and said quantitative determination may be conducted by the methods which are common in the related art. Such quantitative determination methods for FXIIa have been abundantly reported in the literature and the most preferred method for the operator may be adopted. An example of the commonly used methods for determination of FXIIa is a method where the measurement is conducted utilizing the enzymatic activity of FXIIa. The measurement is performed using a substrate to FXIIa. The method using synthetic coloring substrates such as D-Pro-Phe-Arg-pNA, D-Leu-Gly-Arg-pNA and N-Benzoyl-Ile-Glu-Gly-Arg-pNA hydrochloride and methyl ester, and synthetic fluorescent substrates such as Boc-Glu(OBz)-Gly-Arg-MCA and Boc-Gln-Gly-Arg-MCA besides natural substrates such as plasma prekallikrein, blood coagulation factor XI and plasmin is simple and convenient and is commonly and widely used. The above descriptions of the constituting components of the reaction system, the reaction conditions, the measuring methods for determining the produced FXIIa, etc. concerning the present invention are mere examples for conducting the present invention and it is to be understood that the present invention is not limited thereto.

The FXII-activating method using gC1qR in accordance with the present invention can be conducted in various experimental systems. The reaction for activating the FXII plays a very important role as a reaction for controlling the initial stage of various controlling systems for functions in vivo such as the plasma kallikrein-kinin system, blood coagulation system and fibrinolysis system. Therefore, many investigations for the FXII activation have been conducted for elucidating the controlling mechanism in vivo. For example, (1) the elucidation for pathological and physiological significance of the FXII-activating reaction; (2) the study of intrinsic substances existing in living organisms controlling the FXII-activating reaction; and (3) various studies for participation of the FXII activation in several reactions in vivo such as kinin liberation, intrinsic blood coagulation, plasminogen activation and the complement system have been conducted. The method of the present invention whereby the actual FXII-activating reaction in vivo can be reproduced and reflexed in a more faithful or natural manner in the above-mentioned testing and experimental systems is quite useful.

Development of pharmaceuticals having an inhibiting or promoting action towards the plasma kallikrein-kinin system, blood coagulation system, fibrinolysis system, renin-angiotensin system, complement system, arachidonate cascade, etc. in which the FXII activation participates has been conducted as well. For example, a substance which inhibits the plasma kallikrein-kinin system has an inhibitory action upon production of bradykinin which is a final product thereof. Therefore, such a substance is useful as a drug for suppressing pain, inflammation, allergy, etc. induced by bradykinin, such as an analgesic agent, an antiinflammatory agent, an antiallergic agent, etc. In a method of measuring and screening the activity of such a drug, utilization of a reaction system which is nearer to the system in vivo has a higher possibility of finding preferred drugs having a suitable action mechanism. Therefore, the method of the present invention having such a characteristic in vivo-like activation feature can be utilized for measuring the activity of the above-mentioned drugs and is very highly useful. Especially in measuring the activity of a drug which inhibits the FXII activation acting to gC1qR, the method of the present invention is essential.

Specific examples of the method for measuring the activity of the above-mentioned drugs are: (1) a method of measuring the inhibiting activity of a test substance to the production of kallikrein using animal plasma U.S. Pat. No. 4,985,354); (2) a method of measuring the inhibiting and promoting activities of a test substance to the production of FXIIa using animal plasma U.S. Pat. No. 5,599,683); and (3) a method of measuring the inhibiting and promoting activity of a test substance to the production of FXIIa, kallikrein or bradykinin by a reconstituted plasma kallikrein-kinin system U.S. Pat. No. 5,648,228). The disclosures of said Japanese patent publications and U.S. patents are herein incorporated by reference in their entireties.

The present invention is further illustrated by way of the following non-limiting examples wherein all parts, percentages and ratios are by weight and all temperatures are in ° C. unless otherwise indicated:

EXAMPLE 1

PREPARATION OF gC1R.

In the following FXII activating tests, gC1qR which was separated/purified from endothelial cells derived from human umbilical vein (HUVEC) or recombinant gC1qR was used. The recombinant gC1qR used herein is a product prepared by the above-mentioned method by B. Ghebrehiwet, et al. [J. Exp. Med., volume 179, pages 1809–1821 (1994)]. In addition, gC1qR was purified from HUVEC as shown below and subjected to an FXII activating test.

Solubilized HUVEC membrane protein fraction was dialyzed against a 10 mM HEPES buffer containing 159 mM of sodium chloride, 2 mM of phenylmethylsulfonyl fluoride, 1 $\mu$M of aprotinin, 1 $\mu$M of pepstatin, 0.1% of Triton X-100 and 50 $\mu$M of zinc chloride and was added to a HMWK affinity column. After the column was well washed, it was eluted with 0.1 M glycine-HCl (pH: 2.5) and each 0.5 ml of eluates was taken out. Each of the eluates was adjusted to pH 7.0 with 1 M Tris-HCl buffer (pH: 9.0) and subjected to dot blotting by means of a protein-detecting monitor and biotinated HMWK of the eluate whereupon purified gC1qR was obtained.

EXAMPLE 2

TEST OF ACTIVATION OF FXII IN PURE FXII SYSTEM

FXII (20 $\mu$g/ml), 32 $\mu$g/ml of recombinant gC1qR and 0.6 mM of S-2222 (synthetic substrate for FXIIa: N-benzoyl-L-isoleucyl-L-glutamyl-glycyl-L-arginyl p-nitroanilide hydrochloride and methyl ester) were made to react at 25° C. in a HEPES buffer (consisting of 10 mM of HEPES, 137 mM of sodium chloride, 11 mM of D-glucose, 4 mM of potassium chloride, 1 mg/ml of bovine serum albumin, 1 mM of calcium chloride and 50 $\mu$M of zinc chloride; pH: 7.4). The HEPES buffer was treated with (4-amidinophenyl) methanesulfonyl fluoride (APMSF) before use and the proteases contained as contaminants in albumin were inactivated for the sake of safety. p-Nitroaniline was liberated from the synthetic substrate S-2222 by an enzymatic action of FXIIa produced by activation of FXII. Therefore, the amount of FXIIa produced can be determined by measuring the liberated amount of p-nitroaniline. p-Nitroaniline emits yellow light which can be determined by measuring an absorbance at 405 nm. Therefore, said absorbance with lapse of time were monitored using a spectrophotometer to measure the amount of FXIIa produced. An example of the results is shown in FIG. 1 where OD 405 nm is the optical density at 405 nm.

EXAMPLE 3

TEST OF ACTIVATION OF FXII IN RECONSTITUTED PLASMA KALLIKREIN-KININ SYSTEM

Figure 2:
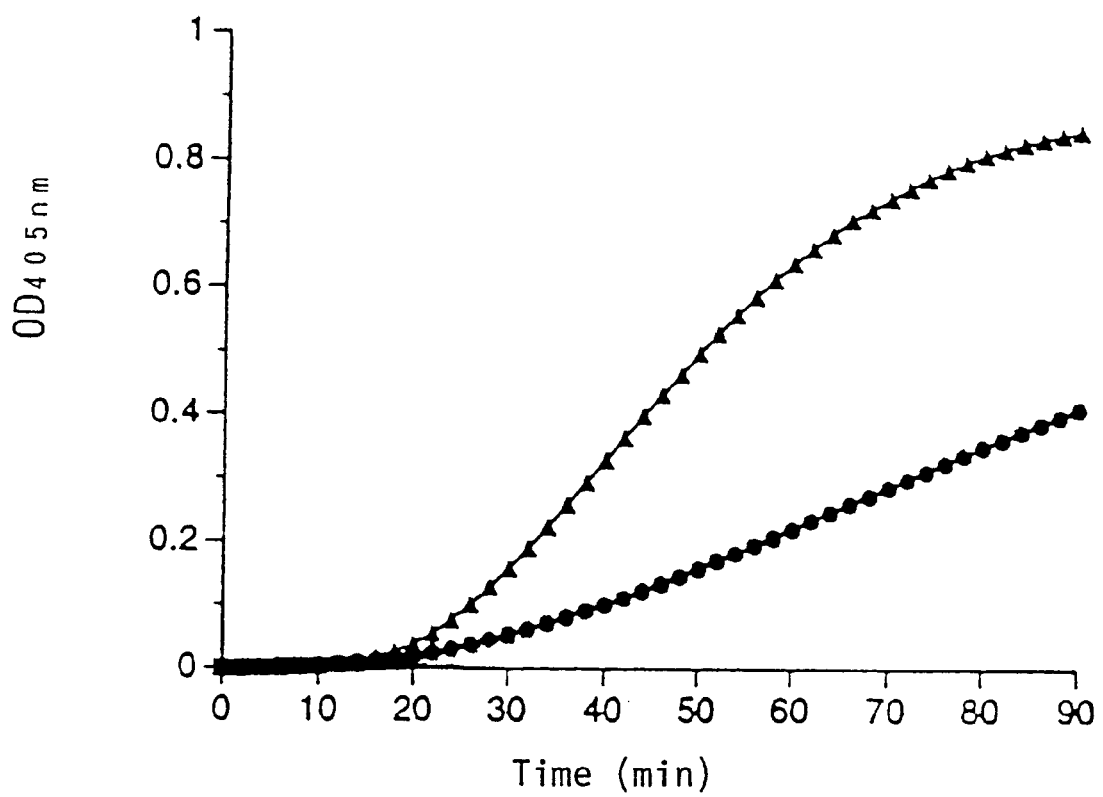
FIG. 2 shows a result of the investigation of Example 3 where activation of FXII by gC1qR was checked at various times in a plasma kallikrein-kinin system which was reconstituted from FXII, plasma prekallikrein and HMWK.

Recombinant gC1qR of various concentrations, 1 $\mu$g/ml of FXII, 1 $\mu$g/ml of HMWK, 1 $\mu$g/ml of plasma prekallikrein and 0.6 mM of S-2302 (a synthetic substrate to plasma kallikrein: H-D-prolyl-L-phenylalanyl-L-arginyl p-nitroanilide dihydrochloride) were made to react at 25° C. in the same APMSF-treated HEPES buffer as described in Example 2 above. In this test system, activation of FXII was measured using the amount of kallikrein produced as an index. Thus, when FXII is activated and is converted to FXIIa, FXIIa acts on plasma prekallikrein and converts it to plasma kallikrein having an enzymatic activity. Therefore, when the amount of kallikrein produced there is measured, it is possible to determine how much the FXII is activated. The amount of kallikrein produced was determined by monitoring the emission of yellow color of p-nitroaniline liberated from the synthetic substrate S-2303 by a hydrolyzing action of kallikrein using a spectrophotometer in the same manner as described in Example 2 above. An example of the results is shown in FIG. 2 where OD 405 nm is the optical density at 405 nm.

The test system of Example 2 is a result of the measurement of activation of FXII by the reaction of gC1qR with pure FXII only. As shown by the results set forth in FIG. 1, the coloration of p-nitroaniline liberated from the synthetic substrate, which is an index for the amount of FXIIa produced, increased with a lapse of time whereby it is clear that gC1qR has an action of activating the FXII. In the absence of zinc ions, said activation of FXII by gC1qR was not noted at all. Further, said FXII-activation was inhibited in a concentration-dependent manner by a C1 inhibitor which is known as an endogenous inhibitor existing in plasma.

The test system of Example 3 is a reconstituted system of a plasma kallikrein-kinin system consisting of FXII, plasma kallikrein and HMWK and is a result where the activation of FXII was measured using the produced amount of kallikrein as an index. As shown by the results set forth in FIG. 2, gC1qR activated the FXII in a concentration-dependent manner and, like the reaction system of Example 2, the activation was not noted in the absence of zinc ions. When the concentration of FXII was varied in this FXII activation reaction system where the amount of gC1qR was made constant, the amount of the produced kallikrein increased dependent on the amount of the FXII utilized. When gC1qR purified from HUVEC as described in Example 1 was used in place of the recombinant gC1qR, the same FXII activation was noted. Accordingly, it was suggested that the saccharized site in gC1qR did not affect the activation of FXII.

As mentioned hereinabove, it has now become clear that the receptor to the globular heads of C1q (gC1qR) has an action of activating the FXII and said receptor is one of the actual FXII-activating substances in vivo. Therefore, the FXII-activating method in accordance with the present invention reproduces and reflects the actual FXII-activating reaction in vivo in a more faithful manner and said method is different from the conventional ones using a heterologous surface having negative charges. The FXII-activating method of the present invention is very highly useful as a method which is capable of conducting the activating reactions in a reaction system nearer the in vivo system. The method for FXII activation using gC1qR may be used in various studies concerning the FXII-activating reaction, and activated FXII. In addition, the FXII activation may be used in methods of measuring the activity and of screening pharmaceutical agents or drugs participating in the reaction systems in vivo, such as a plasma kallikrein-kinin system using said FXII-activation as an initial stage. Use of an isolated or at least substantially purified protein receptor substantially eliminates other factors, such as other cell membrane proteins which may complicate the analysis or interfere or compete with the FXII activation. It facilitates the attainment of clearer data on the inhibitory or promoting effect of test substances, such as drugs upon FXII activation.

We claim:

1. A method for activating blood coagulation factor XII comprising reacting blood coagulation factor XII with a receptor for globular heads of C1q thus producing activated blood coagulation factor XII (FXIIa).

2. A method for activating blood coagulation factor XII according to claim 1 wherein said reacting is conducted in the presence of zinc ions.

3. A method for activating blood coagulation factor XII according to claim 2 wherein said reacting is conducted in animal plasma which contains blood coagulation factor XII.

4. A method for activating blood coagulation factor XII according to claim 2 wherein said reacting is conducted in a reconstituted plasma kallikrein-kinin system.

5. A method for activating blood coagulation factor XII according to claim 2 wherein said reacting is conducted in at least substantially pure blood coagulation factor XII.

6. A method for activating blood coagulation factor XII according to claim 2 wherein said reacting is conducted in the presence of a saccharide.

7. A method for activating blood coagulation factor XII according to claim 1 wherein said receptor is separated, purified, or isolated from cell membranes.

8. A method for the activating blood coagulation factor XII according to claim 7 wherein the membranes comprise membranes of cultured and proliferated cells or tumorigenically transformed cultured cells.

9. A method for activating blood coagulation factor XII according to claim 1 wherein said receptor is prepared by separation and purification from cells selected from the group consisting of endothelial cells, lymphocytes, monocytes, macrophages, neutrophils, eosinophils, fibroblasts, platelets and synovial cells.

10. A method for the activating of blood coagulation factor XII according to claim 9 wherein the receptor is separated from the cells by solubilizing cell membrane and purifying the solubilized cell membrane by chromatography.

11. A method for activating blood coagulation factor XII according to claim 10 wherein said chromatography is affinity chromatography using a carrier obtained by insolubilization of gC1q or high molecular weight kininogen.

12. A method for activating blood coagulation factor XII according to claim 1 wherein said receptor is a recombinant gC1qR.

13. A method for activating blood coagulation factor XII according to claim 1, further comprising quantitatively measuring activated blood coagulation factor XII (FXIIa) produced by said reaction.

14. A method for evaluating a pharmaceutical for inhibiting production of activated blood coagulation factor XII (FXIIa) comprising reacting blood coagulation factor XII with a receptor for globular heads of C1q thus producing activated blood coagulation factor XII (FXIa) in the presence of said pharmaceutical, and quantitatively determining degree of activation of the blood coagulation factor XII as a measure of said pharmaceutical production of FXII, wherein said receptor is obtained by separation, purification, or isolation from cell membranes or is a recombinant gC1qR.

15. A method for evaluating a pharmaceutical according to claim 14 wherein said receptor is prepared by separation and purification from cells selected from the group consisting of endothelial cells, lymphocytes, monocytes, macrophages, neutrophils, eosinophils, fibroblasts, platelets and synovial cells.

16. A method for evaluating a pharmaceutical according to claim 14 wherein the pharmaceutical is screened for utility as an antiinflammatory agent, an antiallergic agent, or an analgesic.

17. A method for evaluating a pharmaceutical for inhibiting production of activated blood coagulating factor XII as claimed in claim 14, wherein said quantitatively determining degree of activation of the blood coagulation factor XII comprises measuring enzymic activity of said FXIIa.

* * * * *